(12) United States Patent
Forster et al.

(10) Patent No.: US 6,273,253 B1
(45) Date of Patent: Aug. 14, 2001

(54) CARTRIDGE AND SYSTEM FOR HOLDING AND APPLYING CLIPS

(75) Inventors: Michel Forster, Le Ruirs (FR);
Lawrence Crainich, Charlestown, NH (US); Wolfgang Eisold, Balghein (DE);
Wayne Knupp, Duxbury, MA (US);
Beate Schoppler, Spaichingen (DE);
Jacques LeBozec, Vitre (FR)

(73) Assignee: Vitalitec International, Inc., Plymouth, MA (US)

( * ) Notice: Subject to any disclaimer, the term of this patent is extended or adjusted under 35 U.S.C. 154(b) by 0 days.

(21) Appl. No.: 09/612,206

(22) Filed: Jul. 7, 2000

(51) Int. Cl.⁷ ..................................... B65D 85/24
(52) U.S. Cl. ...................... 206/339; 206/338; 206/340
(58) Field of Search ..................... 206/338, 339, 206/340; 606/151, 157, 158

(56) References Cited

U.S. PATENT DOCUMENTS

| | | |
|---|---|---|
| 3,713,533 | 1/1973 | Reimels . |
| 3,867,944 | 2/1975 | Samuels . |
| 4,076,120 | 2/1978 | Carrolls et al. . |
| 4,146,130 | 3/1979 | Samuels et al. . |
| 4,212,390 | 7/1980 | Raczkowski et al. . |
| 4,344,531 | 8/1982 | Giersch . |
| 4,696,396 * | 9/1987 | Samuels ............................. 206/339 |
| 4,936,447 | 6/1990 | Peiffer . |
| 4,961,499 | 10/1990 | Kulp . |
| 4,971,198 | 11/1990 | Mericle . |
| 4,972,949 | 11/1990 | Peiffer . |
| 5,046,611 | 9/1991 | Oh . |
| 5,201,416 | 4/1993 | Taylor . |
| 5,279,416 | 1/1994 | Malec et al. . |
| 5,908,430 | 6/1999 | Appleby . |

* cited by examiner

Primary Examiner—David T. Fidei
(74) Attorney, Agent, or Firm—Bachman & LaPointe, P.C.

(57) ABSTRACT

A cartridge for holding clips includes a base and a plurality of walls extending from the base and having wall faces, opposed wall faces of adjacent walls defining a space for receiving a clip, wherein at least one wall of the wall faces has a roughened surface positioned to contact a clip in the space whereby the clip is frictionally held in the space.

19 Claims, 2 Drawing Sheets

CARTRIDGE AND SYSTEM FOR HOLDING AND APPLYING CLIPS

BACKGROUND OF THE INVENTION

The invention relates to a cartridge for holding clips, particularly for holding hemostatic clips for use in surgical procedures.

A great number of disclosures have been made in connection with cartridges for holding hemostatic clips. Examples include U.S. Pat. Nos. 4,076,120, 4,961,499, 5,201,416, 5,908,430 and others. One long standing problem in the industry is a cartridge with structure sufficient to securely hold clips against loss during shipping and the like, which nevertheless allows the clips to be reliably removed without the need for excessive force and the like. Typically, such clips are removed for use by a surgeon during a surgical procedure. It is quite frequent that this maneuver must be accomplished with one hand.

Many of the prior art efforts involve use of extending protrusions and the like which interfere with removal of clips by extending into the path of removal of the clip. This tends to hold clips in place but makes removal of the clip too difficult. Despite the efforts as indicated in the abovementioned and other patents, the need clearly remains for a cartridge for reliably yet readily removably holding clips.

It is therefore the primary object of the present invention to provide a cartridge which securely holds clips in releasable fashion.

Other objects and advantages of the present invention will appear hereinbelow.

SUMMARY OF THE INVENTION

In accordance with the present invention, the foregoing objects and advantages have been readily attained.

In accordance with the invention, a cartridge for holding clips is provided which cartridge comprises a base; a plurality of walls extending from said base and having wall faces, opposed wall faces of adjacent walls defining a space for receiving a clip; wherein at least one wall of said wall faces has a roughened surface positioned to contact a clip in said space whereby said clip is frictionally held in said space.

Still further in accordance with the present invention, a clip applying system is provided which comprises a clip cartridge having a base, a plurality of walls extending from said base and having wall faces, opposed wall faces of adjacent walls defining a space for receiving a clip, wherein at least one wall of said wall faces has a roughened surface positioned to contact a clip in said space whereby said clip is frictionally held in said space; and an applier having jaws for removing clips from said cartridge and applying said clips to an environment of use; wherein a first holding force is defined between said jaws and said clip and a second holding force is defined between said clip and said roughened surface, and wherein said first holding force is greater than said second holding force.

BRIEF DESCRIPTION OF THE DRAWINGS

A detailed description of preferred embodiments of the invention follows, with reference to the attached drawings, wherein.

DETAILED DESCRIPTION

Figure 1:
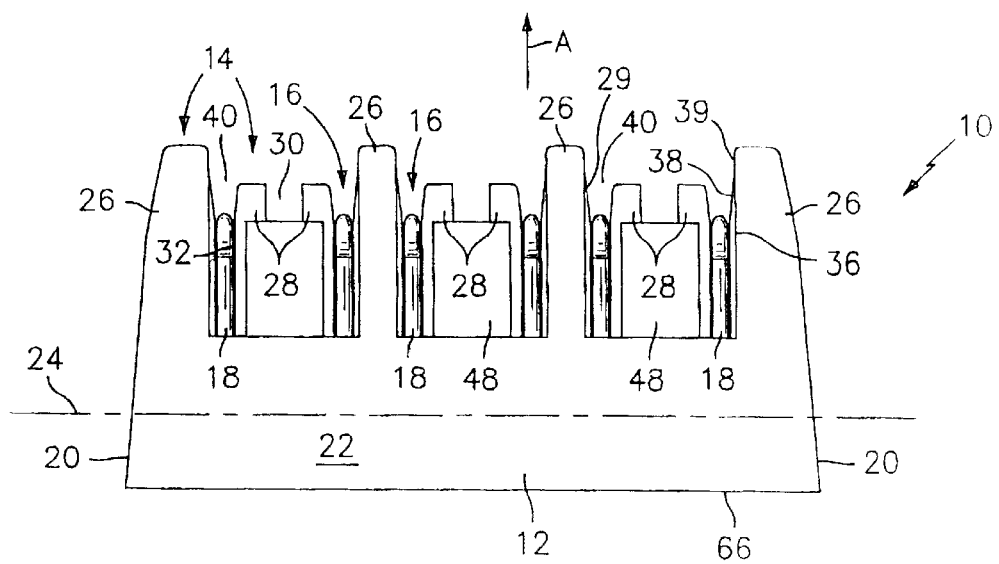
FIG. 1 is a side view of a cartridge in accordance with the present invention.
Figure 2:
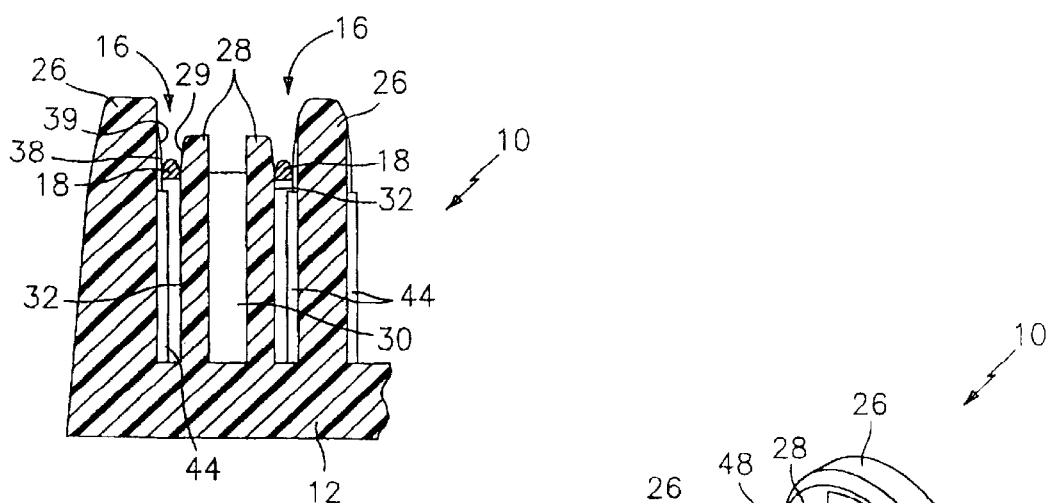
FIG. 2 is a side sectional view of a portion of the cartridge of FIG. 1.
Figure 3:
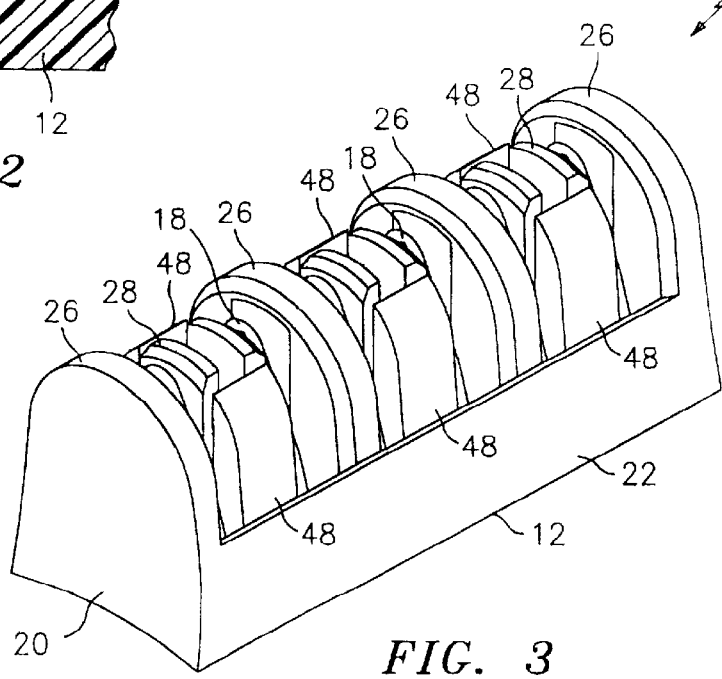
FIG. 3 is a perspective view illustrating the cartridge of FIG. 1.

The invention relates to a cartridge for holding clips, particularly hemostatic clips for use in surgery and the like. Referring to the drawings, FIGS. 1–3 illustrate generally a cartridge 10 in accordance with the present invention.

Cartridge 10 preferably includes a base portion 12 and a plurality of walls 14 extending from base 12 and defining spaces 16 for holding clips 18.

As will be explained below, the cartridge of the present invention advantageously provides for holding clips 18 securely in place in cartridge 10 during shipping and positioning for use without the use of protruding members extending into the path of the clip which tend to make clip removal difficult. Rather, it has been found that a lateral squeezing force applied to clip 18 by a roughened surface or surfaces frictionally holds clips 18 in place while allowing removal when intended. The cartridge of the present invention thereby securely holds clips while nevertheless allowing for convenient removal of the clips when needed by a surgeon.

Base 12 is preferably a substantially elongate structure having ends 20 and sides 22. Walls 14 are preferably positioned transverse to the long dimension of base 12 so as to define spaces 16 in a substantially parallel and side-by-side arrangement as illustrated in FIGS. 1–3. As shown, sides 22 of base 12 are the long dimension of base 12, and a longitudinal axis 24 of base 12 corresponding to this long dimension is also shown in the drawings. Preferably, walls 12 and spaces 16 defined therebetween are substantially perpendicular or transverse to longitudinal axis 24.

Walls 14 preferably include a series of alternating substantially rigid walls 26 and substantially flexible walls 28. Each space 16 is preferably defined between one rigid wall 26 and one flexible wall 28, and flexible walls 28 are preferably formed, manufactured or otherwise provided having a bias slightly toward an opposing rigid wall 26 such that flexible wall 28 applies a lateral holding force to a clip 18 positioned in space 16. Thus, flexible wall 28 has a bias toward a spacing from the opposed wall 26 which is smaller than the width of the clip in space 18. As best illustrated in FIG. 2, walls 14 may advantageously be arranged such that two flexible walls 28 are positioned between each pair of rigid walls 26, with a space 30 defined between adjacent flexible walls 28 so as to allow a flexible wall to be flexed away from rigid wall 26 during loading of cartridge 10 with clips. It should be appreciated, of course, that other arrangements of walls could readily be used well within the scope of the present invention.

Figure 4:
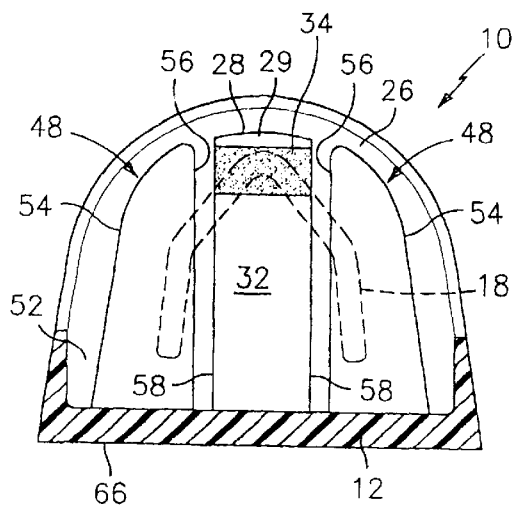
FIG. 4 is a transverse sectional view illustrating the flexible wall portion of a cartridge in accordance with the present invention.

Referring now to FIG. 4, a sectional view taken through cartridge 10 is provided so as to illustrate flexible wall 28 and clip contacting surface 32 thereof. Wall 28 as shown is preferably a smooth wall extending upwardly from the base 12 toward an open or terminal end 40 of space 16. If desired, an upper edge 29 of wall 28 can be tapered away from opposed wall 26 to widen space 16 at open end 40. This facilitates insertion of clips during manufacture loading or assembly, and also facilitates insertion of an applier to remove a clip.

In accordance with the present invention, surface 32 is provided with a roughened portion or surface 34 positioned to contact a clip 18 within a space 16 so as to securely hold clip 18 within space 16 as desired. This roughened surface is advantageously selected in accordance with the present invention to provide a sufficient lateral or frictional hold on clip 18 while nevertheless allowing clip 18 to be removed without difficulty when needed. As will be discussed below, a particular range of roughness or texture for roughened surface 34 has been advantageously found in accordance with the present invention to provide an excellent holding force on clips 18 without interfering with removal of clip 18 when desired.

Figure 5:
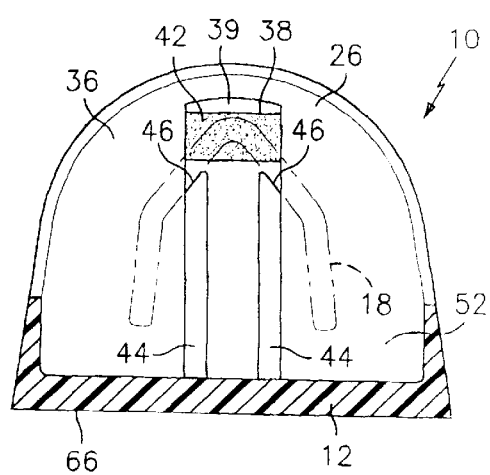
FIG. 5 is a transverse sectional view illustrating the rigid wall portion of a cartridge in accordance with the present invention.

FIG. 5 shows a sectional view illustrating a rigid wall 26. As shown, rigid wall 26 is preferably provided having a substantially flat surface 36 having a raised portion 38 positioned to contact a clip 18 in space 16 as desired in accordance with the invention. Raised portion 38 is preferably a straight-walled portion which extends from base 12 upwardly and away from base 12 and toward open or terminal end 40 of cartridge 10. Raised portion 38 may also be provided with a roughened surface 42 if desired. Raised portion 38 may also have an upper edge 39 which tapers away from opposed flexible wall 28 so as to widen space 16 at open end 40. Thus, walls 26, 28 have extending portions which extend from the clip contacting portion to open end 40. It is preferred that the clip contacting portions corresponding to surfaces 34, 42, when a clip is positioned between them, be substantially straight and parallel, and that the extending portions extend to open end 40 in a direction which is either straight, or tapered away from each other as with edges 29, 39, whereby the clip can be removed from the space with only laterally applied friction and without interference from protruding structures on either wall.

Figure 6:
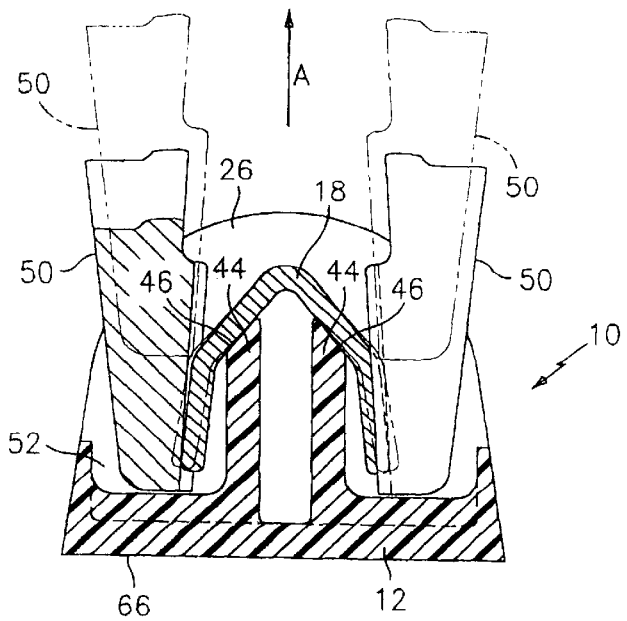
FIG. 6 illustrates positioning of jaws of an applier for use in removing a clip from the cartridge of the present invention.

As shown in FIG. 5, rigid wall 26 is preferably also provided with support members 44 for supporting a clip 18 within space 16 as desired. Support members 44 are preferably spaced structures extending from raised portion 38 for spaced point contact with an inner surface of clip 18. In the embodiment shown in FIG. 5, support members are substantially vertically arranged ridges which terminate at an upper end in support surfaces 46 for contacting clip 18 as desired. FIG. 6 shows a similar view illustrating support members 44 which in this figure are sectioned to further illustrate the structure of same. As shown, members 44 contact two points on the inner surface of clip 18 so as to advantageously provide stable, spaced-point support for clip 18 within space 16 as desired.

As discussed above, roughened surfaces 34, 42 are preferably provided having a particular range of roughness which has been found to be advantageous for holding clips 18 in place without interfering with removal when desired. Roughness of such a surface can advantageously be measured using, for example, a roughness gauge as provided by Charmilles Technologies, and it is preferred in accordance with the present invention that roughened surfaces 34, 42 have a roughness ($R_a$) of between about 18 $\mu$m and about 33 $\mu$m. More preferably, the roughness is between about 21 $\mu$m and about 33 $\mu$m.

The desired roughness can be provided through a number of different techniques. For example, cartridge 10 is preferably injection molded, and the mold from which cartridge 10 is to be manufactured can be treated so as to provide the desired roughened surface, or resulting pieces can be subsequently treated to roughen the surface. It is preferred, of course, that the roughened surfaces be provided through the mold so that an additional step is not needed.

In order to provide the roughened surface, the corresponding surface of the mold is preferably treated so as to roughen that portion of the mold, which will thereby roughen the desired portion of the resulting molded part. The relevant mold surfaces can be treated through electroerosion for roughening same, or can be ground so as to provide the desired roughness. It is preferred in accordance with the present invention that the mold be roughened using electroerosion since this type of roughening process does not result in "directional roughness". As used herein, directional roughness refers to surface roughness which has a greater resistance to sliding motion in one direction than in another. This type of directional roughness frequently results from grinding processes. Grinding processes can nevertheless be used to roughen the desired mold surfaces in accordance with the present invention, provided that the grinding is carried out so as to provide directional roughness which has reduced resistance to sliding in a direction that does not correspond with the direction of removing of a clip from the housing.

FIG. 6 shows jaws of an applier device positioned within housing for removal of clip 18. The structure of cartridge 10 defines a direction for removing this clip in a generally upward direction as illustrated by arrow A. Thus, should the mold for making cartridge 10 of the present invention be ground or otherwise provided with roughness on surfaces 34, 42 which is directional, it is preferred that the mold be ground so as to provide a direction of roughness or direction of reduced resistance to motion which is oriented at an angle with respect to arrow A of at least about 45°. Thus, in accordance with the present invention, roughened surfaces 34, 42 are preferably provided either with non-directional roughness, or with directional roughness wherein the direction of reduced resistance to motion is offset with respect to a removing direction defined by cartridge 10 by at least about 45°.

As best illustrated in FIGS. 3 and 4, cartridge 10 may preferably also be provided with jaw guiding members 48, most preferably laterally spaced to either side of flexible walls 28 substantially as shown. Jaw guiding members 48 are preferably substantially rigid members which are spaced from rigid walls 26 so as to define side-spaces 52, to either side of a clip 18 within space 16, to properly guide jaws 50 of an applier into position for use in removing clip 18 as desired and as illustrated in FIG. 6.

Figure 7:
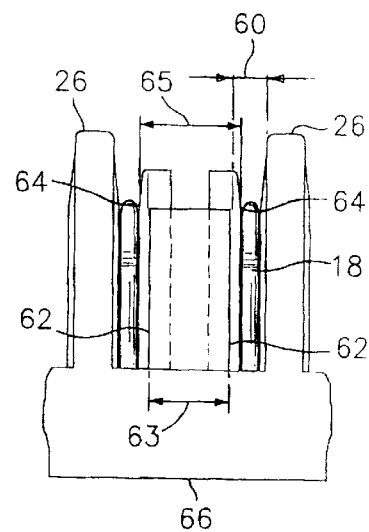
FIG. 7 illustrates a section of a cartridge according to the invention to provide additional details of wall structure thereof.

As best shown in FIG. 4, jaw guiding members 48 may be rounded on their outer edges 54, and may have inner edges 56 which are substantially parallel to side edges 58 of flexible walls 28. As best shown in FIGS. 1 and 7, jaw guiding members 48 define jaw guiding space 52 with a width 60 (FIG. 7) that is greater than the width of clip 18 positioned within space 16. Also as shown in FIG. 1, jaw guiding members 48 may preferably be positioned between pairs of rigid walls 26 and have opposing jaw guiding surfaces 62 each facing a different rigid wall 26.

In the preferred embodiment of the present invention, flexible walls 28 are positioned in adjacent pairs each having a clip-facing surface 64, and it is preferred that the spacing 65 (FIG. 7) between clip-facing surfaces 64 be greater than the spacing 63 between jaw guiding surfaces 62.

A system for applying clips is also provided in accordance with the present invention, and includes cartridge 10 as described and illustrated above, along with an applier having jaws 50 for example as illustrated in FIG. 6. It has been found to be particularly advantageous to provide jaws 50 having clip-contacting portions which, when gripping a clip 18, have a greater relative holding force than does the cartridge holding the clip. The holding force is of course a function of three parameters, namely, coefficient of friction between surfaces, surface area and transverse force. Thus, a greater coefficient of friction between jaws 50 and clip 18 than between clips 18 and roughened surfaces 34, 42 is desired such that clips 18 will be firmly held within cartridge 10 as desired, but can nevertheless be readily removed using jaws 50 as desired.

In addition, the type of roughness of the jaws of the applier has also been found to be important.

As with the mold for cartridges 10, it is preferred that clip grasping portion of jaws 50 be roughened using either electroerosion to obtain non-directional roughness, or that the grasping portions be ground to provide roughness which is directional in an acceptable direction. Since jaws 50 are typically provided with a channel for holding clips, and roughness is most useful in the channel, it is difficult to grind in roughness which is not directional along the length of the channel. Thus, it is best to provide the desired roughness on the jaws using electroerosion.

In further accordance with the invention, base 12 preferably has a flat bottom surface 66 which may advantageously be provided with a sheet or coating of exposable adhesive or the like such that cartridge 10 can be fixed in place on a desired position of use, for example, a surgeon's cart and the like. The particular types of adhesive and covering for such adhesive are materials well known to a person of ordinary skill in the art. This is particularly advantageous since during use of cartridge 10, a surgeon must frequently be able to remove a clip 18 using a single hand. Bottom 66 is advantageously positioned on base 12 so as to support cartridge 10 on a flat working surface with walls 14 extending upwardly and away from the flat working surface.

Alternatively, cartridge 10 can be mounted for use in a heavy base, which is a weighted structure having an upwardly opening dove tail groove in which cartridge 10 can be securely disposed. Still further, other structures could readily be used for stably holding cartridge 10 in place for use by a surgeon to remove clips, well within the scope of the present invention.

Cartridge 10 may preferably be provided as a single molded part, and may be manufactured of polycarbonate, polyamide, or other similar materials which have been found to be excellent materials for cartridge 10 in connection with mechanical elastic performance and stability over time after sterilization processes such as Gamma ray, Ethylene oxide, temperature and so on. The rigid and flexible walls are provided with the desired rigid and flexible nature through the structural formation of same. That is, the rigid walls are preferably a double-walled and enclosed structure which lends stability and rigidity as desired and which defines opposed surfaces each of which defines one rigid wall of a space.

The flexible walls are preferably provided as single-walled structures connected to the base at a portion which serves as a hinge to allow the wall to pivot away from the adjacent rigid wall as desired. This allows insertion of clips during assembly or loading of the cartridge. Further, defining a hinge at the base of the flexible wall serves to define a stable and constant force on clips 18 by maximizing the length of the wall between the hinge and force application point.

This application is related to commonly owned PCT Application No. PCT/FR97/01410, which is incorporated herein in its entirety by reference.

It should readily be appreciated that the cartridge in accordance with the present invention advantageously provides for holding of clips through laterally applied pressure, ideally between one or more roughened surfaces, in a manner which does not position any interfering structure within the outlet space of the cartridge such that a clip can be readily removed by merely overcoming the frictional force of the relative roughness between the clip and roughened surfaces.

It should also readily be appreciated that although each of rigid and flexible walls 26, 28 have been described as having roughened surfaces, it is well within the scope of the present invention for only one or the other of these walls to be provided with a roughened surface.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed:

1. A cartridge for holding clips, comprising:
   a base; and
   a plurality of walls extending from said base and having wall faces, opposed wall faces of adjacent walls defining a space for receiving a clip;
   wherein at least one wall of said wall faces has a roughened surface positioned to contact a clip in said space whereby said clip is frictionally held in said space.

2. The cartridge of claim 1, wherein said roughened surface has a roughness of between about 18 and about 33 µm.

3. The cartridge of claim 1, wherein said roughened surface has a roughness of between about 21 and about 33 µm.

4. The cartridge of claim 1, wherein said clip has two legs extending from a connecting portion, and wherein said roughened surface is positioned to contact said connecting portion.

5. The cartridge of claim 4, wherein said clip is positioned in said space with said legs extending from said connecting portion toward said base.

6. The cartridge of claim 5, wherein at least one of said wall faces defining said space has a support member for supporting a clip in said space with said connecting member contacting said roughened surface.

7. The cartridge according to claim 6, wherein said support member comprises two spaced members positioned for spaced point contact with said clip.

8. The cartridge of claim 1, wherein said walls comprise a plurality of rigid walls and a plurality of flexible walls, each space being defined between a rigid wall and a flexible wall, said flexible wall having a bias toward a spacing from a corresponding rigid wall which is smaller than a width of said clip whereby a lateral holding force is applied to said clip.

9. The cartridge of claim 8, wherein said lateral holding force is applied to said clip by said roughened surface.

10. The cartridge according to claim 8, further comprising two jaw guiding members arranged on each side of said flexible wall, said jaw guiding members being spaced from said rigid walls to define a jaw receiving gap for guiding insertion of jaws for removing a clip from said space.

11. The cartridge according to claim 10, wherein said jaw guiding members each comprise a wall segment extending from said base substantially parallel with said rigid wall and spaced laterally from said flexible wall.

12. The cartridge according to claim 8, wherein said rigid walls have opposed wall faces, and wherein two spaced flexible walls are positioned between each pair of rigid walls whereby one flexible wall of said two spaced flexible walls and one opposed wall face of said opposed wall faces define said space for said clip.

13. The cartridge according to claim 12, further comprising two jaw guiding members arranged on each side of each of said two flexible walls, said jaw guiding members being spaced from said opposed wall faces to define a jaw receiving gap for guiding insertion of jaws for removing a clip from said space.

14. The cartridge according to claim 13, wherein said jaw guiding members have opposed jaw guiding surfaces spaced a first distance from each other and each facing an opposed wall surface to define said jaw receiving gap, wherein said two spaced flexible walls have opposed flexible wall surfaces spaced a second distance from each other and each facing an opposed wall surface, and wherein said second distance is greater than said first distance.

15. The cartridge of claim 1, wherein said at least one wall has a first portion having said roughened surface and a second portion having a roughness which is less than said roughened surface.

16. The cartridge according to claim 1, wherein said base is a substantially elongate member having a long dimension, and said walls are arranged substantially transverse to said long dimension.

17. The cartridge of claim 1, wherein said walls extend from said base to an open end for allowing removal of said clip, wherein said walls have clip contacting portions which are substantially straight and parallel and which include said roughened portion, and wherein said walls have extending portions which extend from said clip contacting portions to said open end in a direction which is one of straight and tapered away from each other whereby said clip can be removed from said space without interference from said walls.

18. The cartridge according to claim 1, wherein the base and walls define a direction of movement of said clip being removed from said space, and wherein said roughened surface has a roughness selected from the group consisting of non-directional roughness and directional roughness having a reduced friction direction which is offset at least about 45° from said direction of movement.

19. A clip applying system, comprising:

a clip cartridge having a base, and a plurality of walls extending from said base and having wall faces, opposed wall faces of adjacent walls defining a space for receiving a clip, wherein at least one wall of said wall faces has a roughened surface positioned to contact a clip in said space whereby said clip is frictionally held in said space; and an applier having jaws for removing clips from said cartridge and applying said clips to an environment of use;

wherein a first holding force is defined between said jaws and said clip and a second holding force is defined between said clip and said roughened surface, and wherein said first holding force is greater than said second holding force.

* * * * *